United States Patent

Bull et al.

[11] Patent Number: 5,491,137
[45] Date of Patent: Feb. 13, 1996

[54] 14α17α-(PROPANO-AND 17²PROPENO)-ESTRATRIENES

[75] Inventors: James R. Bull, Cape Town, South Africa; Walter Elger, Berlin, Germany; Karl-Heinrich Fritzemeier, Berlin, Germany; Rolf Krattenmacher, Berlin, Germany

[73] Assignee: Schering Aktiengesellschaft, Berlin, Germany

[21] Appl. No.: 140,061

[22] PCT Filed: Apr. 30, 1992

[86] PCT No.: PCT/EP92/00946

§ 371 Date: Oct. 29, 1993

§ 102(e) Date: Oct. 29, 1993

[87] PCT Pub. No.: WO92/19642

PCT Pub. Date: Nov. 12, 1992

[30] Foreign Application Priority Data

Apr. 30, 1991 [DE] Germany .......................... 41 14 634.4

[51] Int. Cl.⁶ .............................. A61K 31/56; C07J 1/00
[52] U.S. Cl. .............................. 514/182; 552/510
[58] Field of Search .............................. 552/510; 514/182

[56] References Cited

U.S. PATENT DOCUMENTS 4,789,671  12/1988  Bull et al. .............................. 514/182

FOREIGN PATENT DOCUMENTS

| 2002692 | 5/1990 | Canada . |
| EP-A372665 | 6/1990 | European Pat. Off. . |
| 3808679 | 9/1989 | Germany . |
| WO-A8801275 | 2/1988 | WIPO . |

OTHER PUBLICATIONS

CA 85: 21707, Kumar "Attempted Synthesis . . ." Diss Abstr. Int B 1976, 36(10) 5046–5047.
CA 88: 7191, Szeto "Potential Inhibitors . . . ", Diss Abstr. Int B 1977, 38(3) 1125–1126.

*Primary Examiner*—Johann Richter
*Assistant Examiner*—Catherine S. Kilby Scalzo
*Attorney, Agent, or Firm*—Millen, White, Zelane & Branigan

[57] ABSTRACT

14α,17α-(Propano-and 17²-propeno)-estratrienes of general formula I

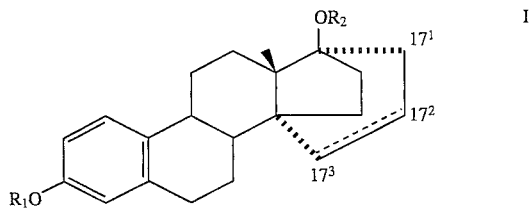

in which

R¹ means a hydrogen atom, a methyl or an acyl group with 1–12 carbon atoms,

R² means a hydrogen atom or an acyl group with 1–12 carbon atoms and

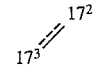

a C—C single or double bond.

The new compounds of general formula I are estrogen effective just as ethinyl estradiol.

6 Claims, No Drawings

14α 17α -(PROPANO-AND 17²PROPENO) -ESTRATRIENES

This is a 371 of EP92/009946 filed Apr. 30, 1992.

The invention relates to new 14α,17α-(propano-and 17²-propeno)-estratrienes of general formula I

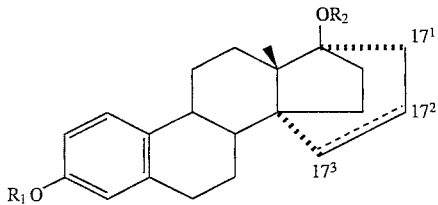

in which

R¹ means a hydrogen atom, a methyl or an acyl group with 1–12 carbon atoms,

R² means a hydrogen atom or an acyl group with 1–12 carbon atoms and

a C—C single or double bond.

As acyl groups $R_1$ and $R_2$, radicals of organic carboxylic acids with 1–12 carbon atoms are suitable. They are derived from aliphatic, cycloaliphatic, aliphatic-cycloaliphatic and aromatic monocarboxylic acids. The number of carbon atoms in the ring varies from 3 to 5. As radicals $R^1$ and $R^2$, the acyl groups of acetic acid, propionic acid, butyric acid, isobutyric acid, pivalic acid, caproic acid, heptanoic acid, caprylic acid, pelargonic acid, decanoic acid, undecanoic acid, dodecanoic acid, 3-cyclopentylpropionic acid and benzoic acid are preferred.

14,17-Ethano-estratrienes are known from International Patent Application WO 88/01275. Although these compounds do not contain a 17α-ethinyl group, they are as estrogen effective as ethinyl estradiol even after oral administration. So far opinion has been that the 17α-ethinyl group is necessary to achieve an oral effectiveness.

It has now been found that the new 14α,17α-(propano- and 17²-propeno)-estratrienes are also effective after oral administration and in this case surpass the effectiveness of ethinyl estradiol, as can be seen from table 1. The compounds of this application also contain no 17α-ethinyl group.

In the Allen-Doisy test, an evaluation of vaginal smears in ovariectomized rats is performed on days 3–5 (d3-d5) after the one-time administration on day 1 (d1 ) of the test substance. The following cycle stages are distinguished:

1=diestrus (leukocytes and nucleated epithelial cells),

2=proestrus (nucleated epithelial cells),

3=estrus (denucleated horny plaques),

4=metestrus (denucleated horny plaques, leukocytes, epithelial cells).

After oral or subcutaneous administration, estrogenically active substances result in the proliferation of the vaginal epithelium and the hornification of superficial cell layers. Regarded as a threshold value, is the amount of an estrogen at which 50% of the animals reach stage 3. Further, estrogens cause an increase of the uterus weight.

The compounds according to the invention can be formulated and used in the same way as ethinyl estradiol. They are processed to the usual forms of pharmaceutical agents with the additives, vehicles, and flavoring substances usual in galenic pharmaceutics according to methods known in the art. For oral administration, tablets, coated tablets, capsules, pills, suspensions or solutions are especially suitable. For parenteral administration, oily solutions, such as, for example, sesame oil or castor oil solutions are especially suitable, which optionally in addition can also contain a diluent, such as, for example, benzyl benzoate or benzyl alcohol.

The active ingredient concentration in the pharmaceutical compositions is a function of the form of administration and the field of use. Thus, for example, capsules or tablets for the treatment of estrogen deficiency symptoms can contain 0.001 to 0.05 mg of active ingredient, oily solutions for intramuscular injection per 1 ml about 0.01 to 0.1 mg of active ingredient and vaginal ointments about 0.1 to 10 mg per 100 ml of ointment. For contraception in the female, the estrogens according to the invention can be used in combination with gestagens. Tablets or coated tablets preferably are to contain 0.003 to 0.05 mg of the estrogen according to the invention and 0.05 to 0.5 mg of a gestagen.

The compounds according to the invention can be used in the case of estrogen deficiency symptoms of the female, such as, for example, amenorrhea, dysmenorrhea, sterility, frigidity, endometritis, colpitis and menopausal symptoms. Further, the compounds can be used as estrogen components in combination preparations with gestagens for contraceptives in the female.

The 14α,17α-(propano-and 17²-propeno)-estratrienes of general formula I

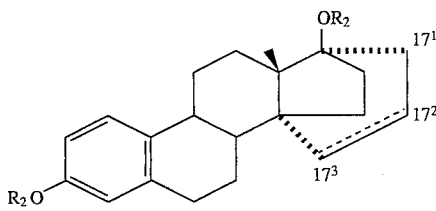

in which

R¹ means a hydrogen atom, a methyl or an acyl group with 1–12 carbon atoms,

R² means a hydrogen atom or an acyl group with 1–12 carbon atoms and

a C—C single or double bond. can be produced with the carbonyl group being reduced in the hydroxy ketone of formula II

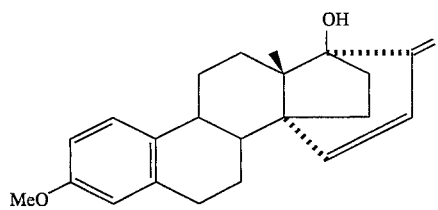

to the methylene group, optionally the 17²–17³ double bond being hydrogenated, optionally the 3-methyl ether being cleaved or the 17-hydroxy group being esterified, optionally the 3-hydroxy group being partially esterified or the 3- and 17-hydroxy groups being simultaneously esterified and optionally a thus obtained 3,17-diacyloxy compound being selectively saponified to the 3-hydroxy-17-acyloxy compound.

The reduction of the carbonyl group to methylene group is performed according to the methods usual in the steroid chemistry.

According to a preferred method the ketone (carbonyl) is first converted into the dethioketal and then reduced with sodium in liquid ammonia. As solvents tetrahydrofuran, dioxane, benzene and toluene are suitable.

The hydrogenation of the $17^2$–$17^3$ double bond takes place in a way known in the art, preferably in the presence of a noble metal catalyst on an inert vehicle.

The optionally subsequent cleavage of a 3-methyl ether is performed according to the usual methods of steroid ether cleavage. Thus, the 3-methyl ether cleavage can, for example, be performed with a Lewis acid in an inert solvent at boiling heat. As Lewis acids, for example, boron trifluoride etherate or diisobutyl aluminum hydride (DIBAH) are suitable. As solvents, benzene, toluene, tetrahydrofuran, dioxane, i.a., are suitable.

The saponification of the acyloxy groups can take place in a way known in the art. For example, the saponification is performed with bases in aqueous alcoholic solution, such as potassium hydroxide in aqueous-methanolic solution.

For the optionally subsequent esterification of the phenolic and tertiary hydroxy group, the processes usually used in steroid chemistry for esterification are suitable. For example, the reaction with acetic acid or aceticanhydride in the presence of strong acids, such as, for example, trifluoroacetic acid, perchloric acid or p-toluenesulfonic acid at room temperature or somewhat elevated temperature or the reaction with aceticanhydride in the presence of a tertiary amine, at about 20°–80° C., can be mentioned.

If pyridine and 4-dimethylamino-pyridine are used together as tertiary amines, the esterification can take place with low carboxylic acids preferably at room temperature and with higher carboxylic acids preferably at 40°–80° C.

The syntheses of the two possible semi-esters take place by partial esterification or partial saponification:

a) Starting from the 3,17-dihydroxy compounds, the 3-acyloxy- 17β-hydroxy compounds can be obtained by selective esterification of the phenolic hydroxy group. The reactions are achieved by reactions of the suitable acid anhydride in the presence of a heterocyclic nitrogen aromatic hydrocarbon, preferably pyridine. As reaction temperature, the range between room temperature and boiling temperature of the reaction mixture is suitable.

b) Starting from 3,17β-diacyloxy compounds, the 3-hydroxy-17α-acyloxy compounds can be obtained by selective saponification of the phenolic acyloxy group. The syntheses take place by reactions with an alkali carbonate or alkaline-earth carbonate, preferably potassium or calcium carbonate, in aqueous-methanolic solution. As reaction temperature, the range between room temperature and boiling temperature of the reaction mixture is suitable.

The production of the initial compound (hydroxyketones of formula II—identical with compound 11—) is described below. The examples after that give a more detailed explanation of the invention.

Production of the initial compounds
3-Methoxy-16-methylestra-l,3,5(10),14,16-pentaen-17-yl acetate (2)

Acetic anhydride (80 ml) and p-toluene sulfonic acid (6 g) are added to a suspension of 3-methoxy-16-methylestra-1, 3,5(10),15-tetraen-17-one (1) (DE-OS 3,023,568 (1982)) (20 g; 67.7 mmol) in isopropenyl acetate (400 ml). The reaction mixture is stirred for about 20 hours at 100° C. After cooling it is poured on ice water and neutralized by addition of small portions of sodium bicarbonate. It is extracted three times with benzene, the combined organic phases are washed with water, dried on magnesium sulfate and concentrated by evaporation in a vacuum. The resulting brown residue (23.5 g) is chromatographed on silica gel with a mixture of ethyl acetate/benzene (1:49). The yellowish crystalline product is further purified by recrystallization of ethyl acetate/methanol. 19.8 g (87%) of colorless 14,16-diene-17-acetate (2) is obtained.

Melting point=129°–130° C.; $[\alpha]^{20}_D$=+259° ($CHCl_3$; c=0.9).

Cycloaddition of phenyl vinyl sulfone to the dienyl acetate (2)

A mixture of dienyl acetate (2) (3.38 g; 10 mmol) and phenyl vinyl sulfone (1.76 g; 10.5 mmol) in absolute xylene (6 ml) is heated in a pressure vessel under nitrogen for 20 hours to 140° C. The thin-layer chromatography shows, in addition to scant initial material, the 3 products (3), (4), (5) [$R_f$-values about 0.38; 0.36; 0.33; mobile solvent: ethyl acetate/toluene (1:9)]. After cooling, the product precipitates with the average $R_f$-value (0.36). The residue is filtered off and crystallized from chloroform/benzene. ($17^2$R-)-3-Methoxy-16-methyl-$17^2$-(phenylsulfonyl)- 14α,17α-ethanoestra-1,3,5(10),15-te traen-17β-yl acetate (4) (720 mg; 14%) is obtained.

Melting point=260°–262° C.; $[\alpha]^{20}_D$=103° ($CHCl_3$; c=0.9)

The filtrate is purified by flash chromatography on silica gel with a mixture of ethyl acetate/benzene (1:19). In addition to contaminated initial material (2) (300 mg), a mixture of cycloadducts (3) and (5) (3.8 g) in a ratio of 1:1 is obtained. A part of this mixture is again chromatographed on silica gel; syrupy 3-methoxy-$17^1$-methyl-16α-(phenylsulfonyl)-14α,17α-ethenoestra- 1,3,5(10)-trien-17β-yl acetate (3) is obtained.

$[\alpha]^{20}_D$=+61° ($CHCl_3$; c=0.1); IR ($CHCl_3$); 1735 cm$^{-1}$.

Reductive desulfonation of the cycloadducts (3) and (5)

A mixture of the cycloadducts (3) and (5) (approximately 1:1) (22.26 g; 44 mmol) is dissolved in a mixture of absolute tetrahydrofuran (80 ml) and absolute methanol (320 ml). After addition of sodium bicarbonate the reaction mixture is cooled to 0° C. Sodium amalgam (6%; 83 g) is added under vigorous stirring. After 2 hours more sodium amalgam (29 g) is added. It is allowed to stir for another 2 hours at 0° C., as well as 16 hours at 25° C. Then, for the destruction of excess reagent, water (50 ml) is carefully added and the mixture concentrated by evaporation under reduced pressure to approximately ⅓ of the volume. Another 300 ml of water is added and it is extracted with chloroform. The organic phase is washed with water and dried on magnesium sulfate. It is concentrated by evaporation in a vacuum and the resulting residue (13 g) is purified by column chromatography on silica gel with a mixture of ethyl acetate/benzene (1:9). 3-Methoxy- $17^1$-methyl-14α,17α-ethenoestra-1,3, 5(10)-trien-17β-ole (6) (11.5 g; 81%) is obtained.

Melting point=147°–149° C. (after crystallization from aqueous methanol); $[\alpha]^{20}_D$=129° ($CHCl_3$; c=0.8)

3-Methoxy-$17^1$-methyl-14α,17α-ethenoestra-1,3,5(10)-trien-17β-yl acetate (7)

p-Toluene sulfonic acid (200 mg) is added with stirring to a suspension of compound 6 (2 g; 6.2 mmol) in acetic anhydride (10 ml) at 0° C. First a clear solution develops, from which a precipitate slowly precipitates. Water is added after one hour, the precipitate is filtered off and chromatographed on silica gel with benzene as mobile solvent. 2.06 g (91%) of compound (7) is obtained.

Melting point=117°–119° C. (after crystallization from dichloromethane/methanol); $[\alpha]^{20}_D$=+87° ($CHCl_3$; c=0.9).

Hydroxylation of the acetoxy-olefin (7)

Osmium tetroxide is added to a solution of compound 7 (586 mg; 1.6 mmol) in absolute pyridine (10 ml). It is allowed to stir for 48 hours more at 25° C., cooled to 0° C. and aqueous sodium disulfite solution (10%; 20 ml) is added. It is stirred for another 30 minutes and then extracted with benzene. The thus obtained crude product (690 mg) is chromatographed on silica gel with a mixture of ethyl acetate/benzene (1:7). $(17^1S,17^2S)$-$17^1,17^2$-Dihydroxy-3-methoxy-$17^1$-methyl-14α,17α-ethanoestra-1,3,5(10)-trien-17β-yl acetate (8) (527 mg; 82%) is obtained.

Melting point=209°–210° C. (after crystallization from benzene/hexane); $[α]^{20}_D$=+16° (CHCl$_3$; c=0.85); IR (CHCl$_3$): 3600–3250 (OH) and 1710 (OAc) cm$^{-1}$.

Further elution with ethyl acetate/benzene (1:4) yields $(17^1R,17^2R)$-14α,17α-ethano-$17^1,17^2$-dihydroxy-3-methoxy-$17^1$-methylestra-1,3,5(10)-trien-17β-yl acetate (9) (45 mg; 7%).

Melting point=169°–170° C. (after crystallization from benzene/hexane); $[α]^{20}_D$=+31° (CHCl$_3$; c=0.9); IR (CHCl$_3$): 3690 and 3550–3150 (OH) and 1710 (OAc) cm$^{-1}$.

17β-(Acetoxy)-3-methoxy-20-oxo-19-nor-17α-pregna-1,3,5(10)-triene-14-carbaldehyde (10)

An aqueous sodium periodate solution (6%, 3 ml) is added to a suspension of diol (8) (100 mg; 0.25 mmol) in ethanol (10 ml) at 25° C. under stirring. It is allowed to stir further for 6 hours at 25° C. Then it is concentrated by evaporation in a vacuum to half the volume, mixed with water and extracted with chloroform. The organic phase is washed with saturated sodium chloride solution, dried on magnesium sulfate and concentrated by evaporation in a vacuum. The obtained crude product is purified by crystallization from ethyl acetate. 94 mg of compound 10 is obtained.

Melting point=212°–213° C.; $[α]^{20}_D$=+3.5° (CHCl$_3$; c=0.85); IR (CHCl$_3$): 1736 (OAc) and 1715 br. (14$^l$-and 20-C=O) cm$^{-1}$.

17β-Hydroxy-3-methoxy-14α,17α-(17²-propeno)estra-1,3,5(10)-trien-$17^1$-one (11)

A solution of compound 10 (430 mg, 1.08 mmol) in stirred in a 1 molar methanolic potassium hydroxide solution (10 ml) for 3 hours at 25° C. Then water is added and it is extracted with toluene. The organic phase is washed with saturated sodium chloride solution and dried on magnesium sulfate. It is concentrated by evaporation in a vacuum and the resulting crude product is purified by crystallization from chloroform/methanol. 114 mg of 17-hydroxy ketone (11) is obtained.

Melting point=170°–180° C.; $[α]^{20}_D$=+195° (CHCl$_3$; c=0.8); IR (CHCl$_3$): 3460 and 1670 cm$^{-1}$.

Column chromatography of the residue of the mother liquor on silica gel with ethyl acetate/toluene (1:9) as mobile solvent yields another 197 mg of compound 11.

3-Methoxy-14α,17α-($17^1$-oxo-$17^2$-propeno)estra-1,3,5(10)-trien-17β-yl acetate (13)

a) Oxoaldehyde 10 (250 mg; 0.63 mmol) is stirred with concentrated hydrochloric acid (1 ml) in tetrahydrofuran (10 ml) for 3 hours at 50° C. Then the reaction solution is neutralized with aqueous sodium bicarbonate solution and extracted with toluene. The organic phase is washed with saturated sodium chloride solution and dried on magnesium sulfate. It is concentrated by evaporation in a vacuum and the resulting crude product is purified by column chromatography on silica gel with ethyl acetate/toluene as mobile solvent. 234 mg of acetoxy ketone 13 is obtained.

Melting point=200°–204° C. (after crystallization from chloroform/methanol); $[α]^{20}_D$=+174° (CHCl$_3$; c=1.0); IR (CHCl$_3$): 1739 and 1693 cm$^{-1}$.

b) Acetic anhydride as well as p-toluene sulfonic acid are added to a solution of hydroxy ketone 11 (150 mg) in toluene (6 ml) at 25° C. It is stirred for 4 hours at 25° C., then neutralized with aqueous sodium bicarbonate solution and extracted with toluene. The organic phase is washed with saturated sodium bicarbonate solution and saturated sodium chloride solution and dried on magnesium sulfate. It is concentrated by evaporation in a vacuum and the resulting crude product is purified by column chromatography on silica gel with a mixture of ethyl acetate/toluene. 149 mg of compound 13 is obtained.

Melting point:=200°–204° C.

EXAMPLE 1

3-Methoxy-14α,17α-($17^2$-propeno)estra-1,3,5(10)-trien-17β-ol (15)

Compound 11 (466 mg; 1.4 mmol) is dissolved in glacial acetic acid (3 ml). It is mixed with ethanedithiol (1 ml) and then boron trifluoride-diethylether complex (120 µl) is added in three equal portions over a time period of 30 hours at 30° C. Then the reaction mixture is poured on aqueous sodium bicarbonate solution. It is extracted with toluene, the organic phase is washed with saturated sodium chloride solution and dried on magnesium sulfate. It is concentrated by evaporation in a vacuum and the resulting crude product is purified by column chromatography on silica gel with a mixture of ethyl acetate/toluene (1:9). 560 mg of thioketal (14) is obtained. IR 3481 cm$^{-1}$ Compound 14 (350 mg; 0.85 mmol) is dissolved in absolute tetrahydrofuran and added with stirring to a mixture of sodium (195 mg) in liquid ammonia (60 ml). It is further stirred for approximately 2 hours at –33° C. After addition of solid ammonium chloride, the ammonia is then allowed to evaporate. The residue is mixed with water. It is extracted with toluene, the organic phase is washed with saturated sodium chloride solution, dried on magnesium sulfate and concentrated by evaporation in a vacuum. The resulting crude product is purified by column chromatography on silica gel with a mixture of ethyl acetate/toluene (1:19). 230 mg of 14α,17α-propeno-compound 15 is obtained.

Melting point=141°–142° C. (after crystallization from chloroform/methanol); $[α]^{20}_D$=+137° (CHCl$_3$; c=0.1); IR (CHCl$_3$): 3603 cm$^{-1}$.

EXAMPLE 2

14α,17α-($17^2$-Propeno)estra-1,3,5(10)-triene-3,17β-diol (16) Diisobutyl aluminum hydride (1 molar in hexane; 3.5 ml; 3.5 mmol) is added to a solution of compound 15 (110 mg; 0.34 mmol) in absolute toluene (5 ml). Then it is refluxed for 24 hours. After cooling to room temperature, it is acidified with dilute hydrochloric acid. It is extracted with methanol/chloroform (1:9), dried on magnesium sulfate and concentrated by evaporation in a vacuum. The thus obtained crude product is purified by column chromatography on silica gel with a mixture of ethyl acetate/toluene (1:4). 90 mg of diol 16 is obtained.

Melting point=156°–159° C. (after crystallization from ethyl acetate); $[α]^{20}_D$=+150° (C=0.9; tetrahydrofuran); MS: m/e=310 (M$^+$).

EXAMPLE 3

3-Methoxy-14α,17α-propanoestra-1,3,5(10)-trien-17β-ol (17) Compound 15 (175 mg) is dissolved in ethyl acetate and hydrogenated in the presence of a palladium-activated carbon (10%; 40 mg) at 1.3 atm. water pressure for 30 hours.

Then it is filtered off and concentrated by evaporation in a vacuum. The thus resulting crude product is purified by column chromatography on silica gel with a mixture of ethyl acetate/toluene. 170 mg of compound 17 is obtained.

Melting point=155°–157° C. (after crystallization from chloroform/methanol); $[\alpha]^{20}_D$=+86 (CHCl$_3$; c=0.9); IR (CHCl$_3$): 3602 cm$^{-1}$.

EXAMPLE 4

14α,17α-Propanoestra-1,3,5(10)-triene-3,17β-diol (18) Diisobutyl aluminum hydride (1 molar in hexane; 3.2 ml; 3.2 mmol) is added to a solution of compound 17 (105 mg; 0.32 mmol) in absolute toluene (5 ml). It is refluxed for 24 hours. After cooling to room temperature, it is acidified with dilute hydrochloric acid and extracted with methanol/chloroform (1:9). It is concentrated by evaporation in a vacuum and the crude product is purified by column chromatography on silica gel with a mixture of ethyl acetate/toluene (3:7). 61 mg of compound 18 is obtained.

Melting point=228°–231° C. (after crystallization from ethyl acetate); $[\alpha]^{20}_D$=+87° (c=0.6; tetrahydrofuran).

The following reaction diagrams illustrate the production of the compounds according to the examples and the initial compounds needed for them:

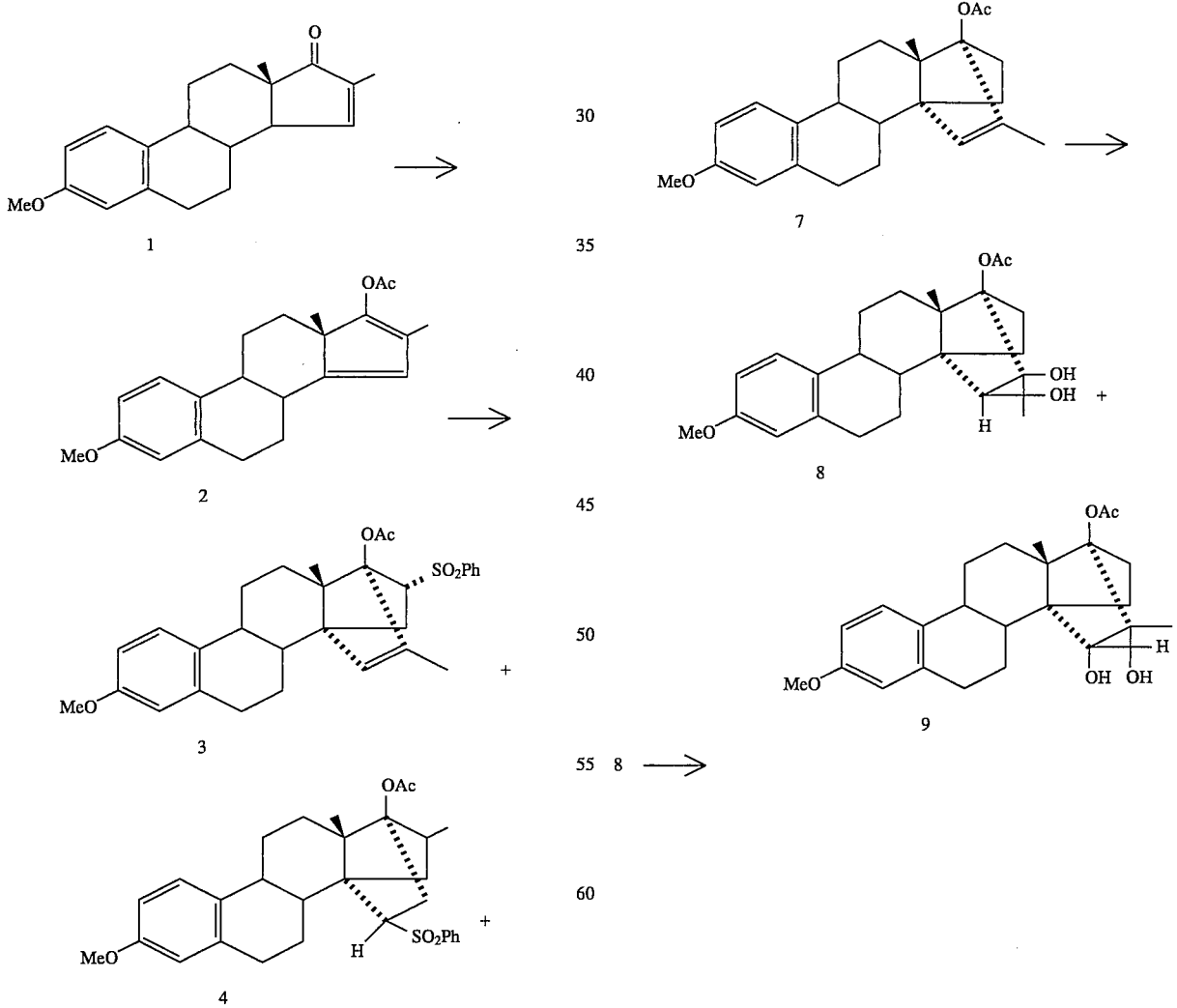

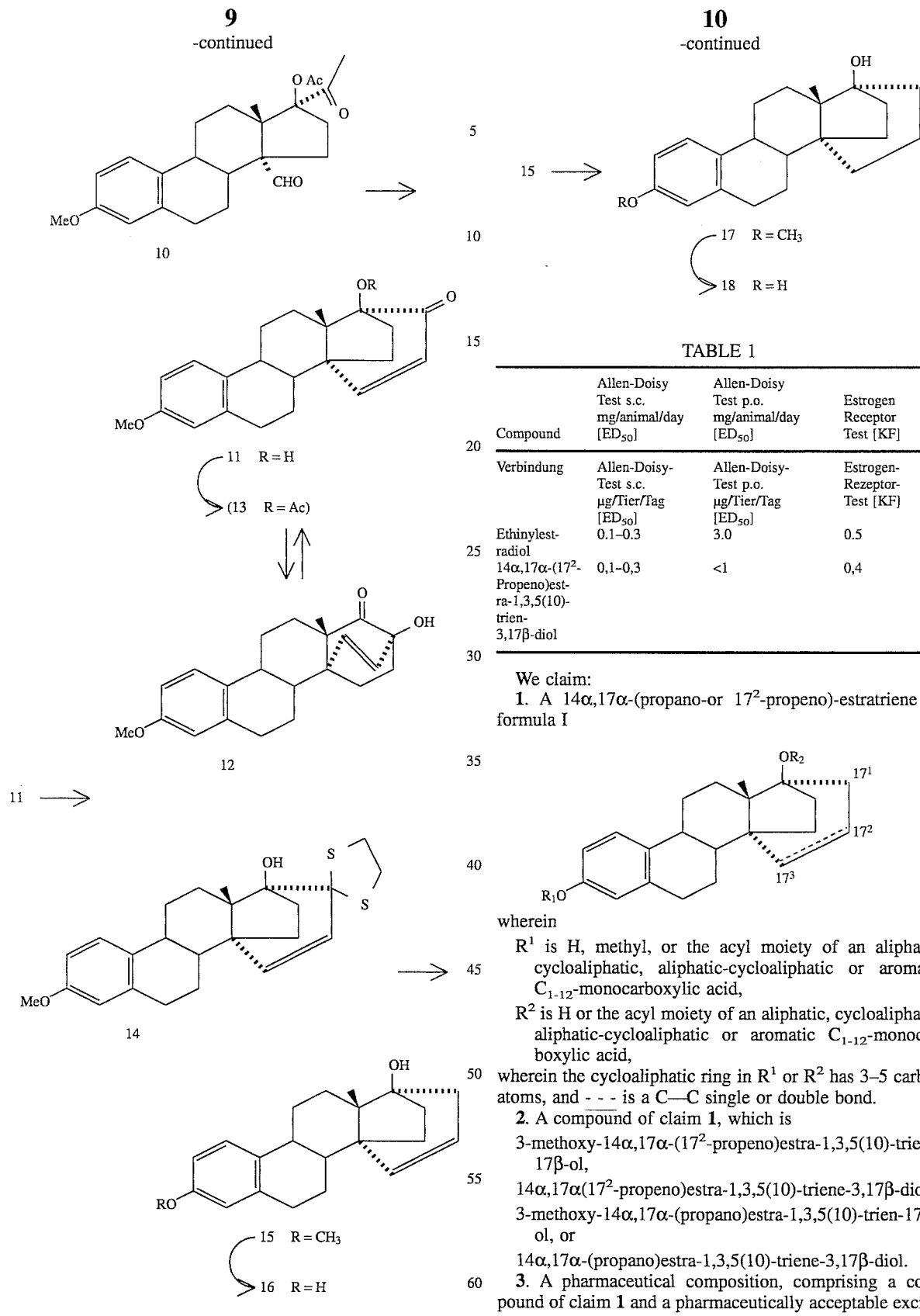

TABLE 1

| Compound | Allen-Doisy Test s.c. mg/animal/day [ED$_{50}$] | Allen-Doisy Test p.o. mg/animal/day [ED$_{50}$] | Estrogen Receptor Test [KF] |
|---|---|---|---|
| Verbindung | Allen-Doisy-Test s.c. μg/Tier/Tag [ED$_{50}$] | Allen-Doisy-Test p.o. μg/Tier/Tag [ED$_{50}$] | Estrogen-Rezeptor-Test [KF] |
| Ethinylestradiol | 0.1–0.3 | 3.0 | 0.5 |
| 14α,17α-(17$^2$-Propeno)estra-1,3,5(10)-trien-3,17β-diol | 0,1–0,3 | <1 | 0,4 |

We claim:

1. A 14α,17α-(propano-or 17$^2$-propeno)-estratriene of formula I wherein $R^1$ is H, methyl, or the acyl moiety of an aliphatic, cycloaliphatic, aliphatic-cycloaliphatic or aromatic $C_{1-12}$-monocarboxylic acid, $R^2$ is H or the acyl moiety of an aliphatic, cycloaliphatic, aliphatic-cycloaliphatic or aromatic $C_{1-12}$-monocarboxylic acid, wherein the cycloaliphatic ring in $R^1$ or $R^2$ has 3–5 carbon atoms, and - - - is a C—C single or double bond.

2. A compound of claim 1, which is 3-methoxy-14α,17α-(17$^2$-propeno)estra-1,3,5(10)-trien-17β-ol, 14α,17α(17$^2$-propeno)estra-1,3,5(10)-triene-3,17β-diol, 3-methoxy-14α,17α-(propano)estra-1,3,5(10)-trien-17β-ol, or 14α,17α-(propano)estra-1,3,5(10)-triene-3,17β-diol.

3. A pharmaceutical composition, comprising a compound of claim 1 and a pharmaceutically acceptable excipient.

4. A pharmaceutical composition, comprising a compound of claim 2 and a pharmaceutically acceptable excipient.

5. A method of treating estrogen deficiency symptoms in a female in need of such treatment, comprising administering an estrogenically effective amount of a compound of claim 1.

6. A method of treating estrogen deficiency symptoms in a female in need of such treatment, comprising administering an estrogenically effective amount of a compound of claim 2.

* * * * *